United States Patent
Kameyama et al.

(10) Patent No.: US 9,464,186 B2
(45) Date of Patent: Oct. 11, 2016

(54) RESIN COMPOSITION, HARDENED COATING FILMS THEREFROM, AND PHOTOSEMICONDUCTOR DEVICE USING SAME

(75) Inventors: Atsushi Kameyama, Tokyo (JP); Takashi Suzuki, Tokyo (JP); Ryuichi Ueno, Tokyo (JP); Isao Ishikura, Tokyo (JP)

(73) Assignee: JX NIPPON OIL & ENERGY CORPORATION, Tokyo (JP)

( * ) Notice: Subject to any disclaimer, the term of this patent is extended or adjusted under 35 U.S.C. 154(b) by 284 days.

(21) Appl. No.: 14/009,909

(22) PCT Filed: Apr. 5, 2012

(86) PCT No.: PCT/JP2012/059394
§ 371 (c)(1),
(2), (4) Date: Jan. 15, 2014

(87) PCT Pub. No.: WO2012/137880
PCT Pub. Date: Oct. 11, 2012

(65) Prior Publication Data
US 2014/0128510 A1  May 8, 2014

(30) Foreign Application Priority Data
Apr. 8, 2011 (JP) ................. P2011-086409

(51) Int. Cl.
| | |
|---|---|
| H01L 33/56 | (2010.01) |
| C08L 63/00 | (2006.01) |
| C08G 59/24 | (2006.01) |
| C08G 59/42 | (2006.01) |
| C08K 5/52 | (2006.01) |
| H01L 23/29 | (2006.01) |
| C07D 493/04 | (2006.01) |
| C08G 59/40 | (2006.01) |
| C08K 5/13 | (2006.01) |
| C08G 59/02 | (2006.01) |

(52) U.S. Cl.
CPC ............... *C08K 5/52* (2013.01); *C07D 493/04* (2013.01); *C08G 59/022* (2013.01); *C08G 59/027* (2013.01); *C08G 59/24* (2013.01); *C08G 59/4071* (2013.01); *C08G 59/42* (2013.01); *C08K 5/13* (2013.01); *C08L 63/00* (2013.01); *H01L 23/293* (2013.01); *H01L 23/296* (2013.01); *C08L 2205/02* (2013.01); *H01L 2924/0002* (2013.01)

(58) Field of Classification Search
None
See application file for complete search history.

(56) References Cited

U.S. PATENT DOCUMENTS

| | | | |
|---|---|---|---|
| 2003/0059618 A1 | 3/2003 | Takai | |
| 2005/0215749 A1 | 9/2005 | Miyake et al. | |
| 2006/0105111 A1 | 5/2006 | Watanabe | |
| 2006/0194063 A1 | 8/2006 | Murai et al. | |
| 2007/0179256 A1* | 8/2007 | Kitao ................ | C07D 303/34 525/523 |
| 2010/0094030 A1* | 4/2010 | Bell .................... | C07D 405/04 549/523 |

FOREIGN PATENT DOCUMENTS

| | | | |
|---|---|---|---|
| CN | 1458927 A | 11/2003 | |
| CN | 1842557 A | 10/2006 | |
| CN | 1852932 A | 10/2006 | |
| EP | 2039692 A1 * | 3/2009 | ........... C07D 303/04 |
| JP | 02-115217 A | 4/1990 | |
| JP | 2004-182648 A | 7/2004 | |
| JP | 2005-68303 A | 3/2005 | |
| JP | 2005-146038 A | 6/2005 | |

(Continued)

OTHER PUBLICATIONS

Chinese Office Action issued with respect to application No. 201280015297.8, mail date is Jan. 6, 2015.
The Journal of Organic Chemistry vol. 65 No. 25, Dec. 15, 2000, pp. 8651-8658.

(Continued)

*Primary Examiner* — Michael J Feely
(74) *Attorney, Agent, or Firm* — Greenblum & Bernstein, P.L.C.

(57) ABSTRACT

A resin composition prepared by blending an epoxy compound represented by the following formula (1), an acid anhydride, and a curing accelerator, wherein the epoxy compound is purified in such a way that, in a chromatogram obtained by gas chromatographic analysis, a ratio of a peak area B of peaks derived from a heavier molecular mass portion having longer retention times than the epoxy compound to a peak area A of peak(s) derived from the epoxy compound B/A is $2.0 \times 10^{-3}$ or less.

[Chemical Formula 1]

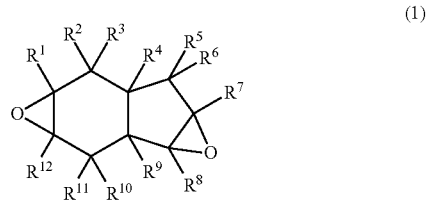

(1)

[In the formula, $R^1$, $R^2$, $R^3$, $R^4$, $R^5$, $R^6$, $R^7$, $R^8$, $R^9$, $R^{10}$, $R^{11}$, and $R^{12}$ each independently represent a hydrogen atom, a halogen atom, an alkyl group which may have a substituent, or an alkoxy group which may have a substituent.].

18 Claims, 2 Drawing Sheets

(56) References Cited

FOREIGN PATENT DOCUMENTS

| JP | 2005-206672 A | 8/2005 |
| JP | 2005-298616 A | 10/2005 |
| JP | 2008-189709 A | 8/2008 |
| JP | 2009-246569 A | 10/2009 |
| JP | 2009-249569 A | 10/2009 |
| JP | 2010-215924 A | 9/2010 |
| JP | 2010-235649 A | 10/2010 |
| TW | I298065 | 6/2008 |
| WO | 2006/054461 A1 | 5/2006 |

OTHER PUBLICATIONS

Organic Syntheses vol. 74, 1997.
Organic Syntheses Collective vol. 9, A Revised Edition of vol. 70-74.
Search Report from International Application No. PCT/JP2012/059394, mail date is Jun. 19, 2012.
International Preliminary Report on Patentability PCT/JP2012/059394, mail date is Oct. 17, 2013.
Office Action issued in Taiwan Counterpart Patent Appl. No. 101112328, dated Aug. 6, 2015.

* cited by examiner

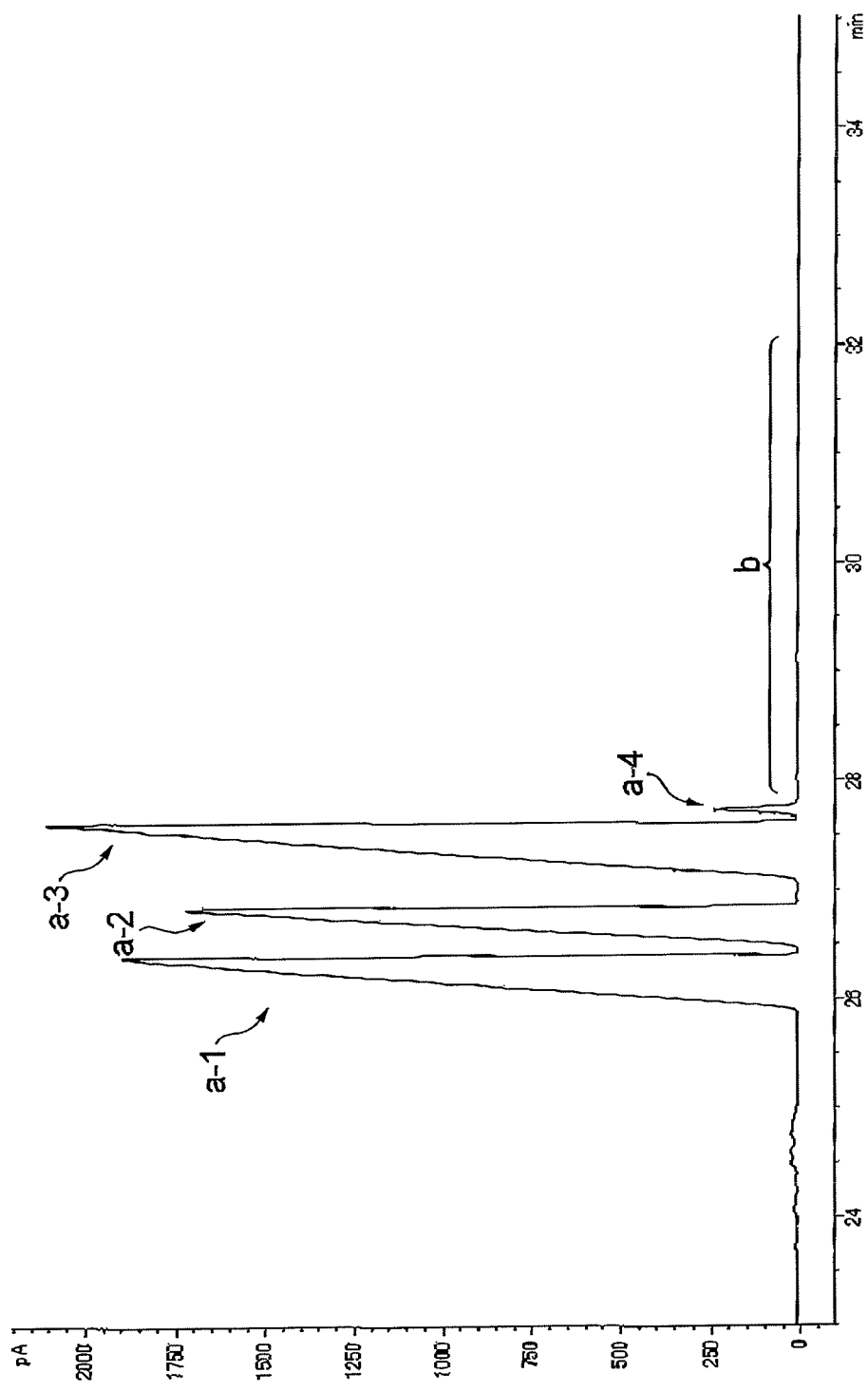

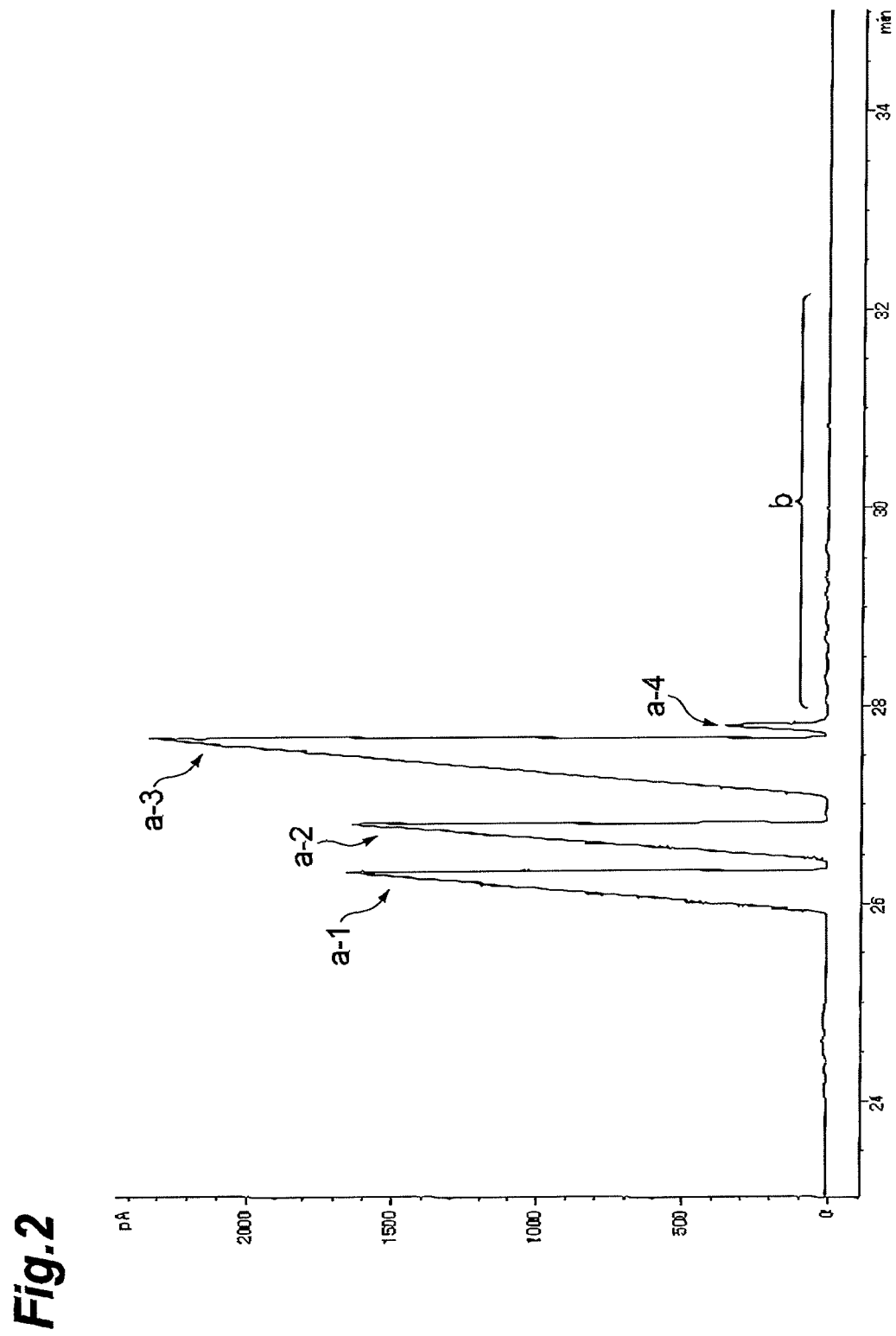

RESIN COMPOSITION, HARDENED COATING FILMS THEREFROM, AND PHOTOSEMICONDUCTOR DEVICE USING SAME

TECHNICAL FIELD

The present invention relates to a resin composition containing an epoxy compound, a cured product thereof, and a photosemiconductor device using the same.

BACKGROUND ART

In recent years, photosemiconductor devices such as a light emitting element like a light emitting diode (LED) or the like that is put to practical use for various display boards, light sources for image reading, traffic signals, units for a large size display and so on, and a light receiving element and the like have been produced for the most part by using sealing resins. Epoxy resins are generally used as such resins for sealing because of being excellent in heat resistance, adhesive properties, humidity resistance, mechanical strength, electrical properties, and so on.

In the past, bisphenol based diglycidyl ethers and phenol based novolac type epoxy resins have generally been used as a sealing material (see, for example, Patent Literature 1). However, the case where a nitride based LED having a light emitting wavelength in the range from blue color to near infrared region that has been put to practical use in recent years is sealed by these conventional epoxy resins causes a problem that an aromatic ring in the epoxy resin absorbs short wavelength light thereby causing a yellowing and the emission intensity of the LED decreases remarkably.

By the way, in the past, it has been known that tetrahydroindene is generated as a by-product in synthesizing vinyl norbornene by the reaction of cyclopentadiene with 1,3-butadiene. And in recent years, an effective utilization method of this tetrahydroindene has been needed.

In Patent literature 2, for example, a method for producing a diepoxide of tetrahydroindene that is an epoxy compound having two cycloaliphatic skeletons within the molecule from tetrahydroindene is disclosed.

In Patent Literature 3, using a thermosetting resin composition, as a substitute for a glass substrate, prepared by blending (A) a non-ester type alicyclic epoxy compound, (B) an epoxy compound that is different from the above (A), and (C) a cationic polymerization initiator by a prescribed amount is disclosed, and a diepoxide of tetrahydroindene is illustrated as an example as (A) a non-ester type aliphatic epoxy compound.

CITATION LIST

Patent Literature

Patent Literature 1: Japanese Patent Application Laid-Open No. 2005-298616
Patent Literature 2: Japanese Patent Application Laid-Open No. 2004-182648
Patent Literature 3: Japanese Patent Application Laid-Open No.

SUMMARY OF INVENTION

Technical Problem

An object of the present invention is to provide a cured alicyclic epoxy resin product having a sufficient optical transparency to not only visible light but also ultraviolet light, a resin composition for obtaining the cured resin product, and a photosemiconductor device sealed by using the resin composition.

Solution to Problem

The present invention relates to a resin composition prepared by blending an epoxy compound represented by the following formula (1), an acid anhydride, and a curing accelerator, wherein the above epoxy compound is purified in such a way that, in a chromatogram obtained by gas chromatographic analysis, a ratio of a peak area B of peaks derived from a heavier molecular mass portion having longer retention times than the above epoxy compound to a peak area A of peak(s) derived from the above epoxy compound B/A is $2.0 \times 10^{-3}$ or less.

[Chemical Formula 1]

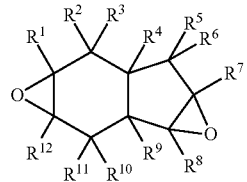

(1)

[In the formula, $R^1$, $R^2$, $R^3$, $R^4$, $R^5$, $R^6$, $R^7$, $R^8$, $R^9$, $R^{10}$, $R^{11}$, and $R^{12}$ each independently represent a hydrogen atom, a halogen atom, an alkyl group which may have a substituent, or an alkoxy group which may have a substituent.]

According to such a resin composition, a cured resin product having a sufficient optical transparency to not only visible light but also ultraviolet light is obtained. Therefore, the above resin composition can preferably be used for use as a sealing material or the like to seal a photosemiconductor element.

In addition, it is a thermosetting resin composition used as a substitute for a glass substrate used for liquid crystal panels or the like that is described in Patent Literature 3, optical transparency to light other than visible light (ultraviolet light, for example, such as UV-A (315 to 400 nm)) is not necessarily needed in such a field. Therefore, in Patent Literature 3, an evaluation of optical transparency for light other than visible light is not conducted, and suggestion or the like to obtain transparency for ultraviolet light is not done. Furthermore, in Patent Literature 3, an example in which a diepoxide of tetrahydroindene was used is described, however the example is inferior to other examples in optical transparency.

The above epoxy compound in the resin composition of the present invention is preferably a compound represented by the following formula (1-1).

[Chemical Formula 2]

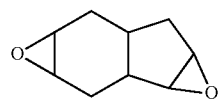

(1-1)

The resin composition of the present invention may also be prepared by further blending an antioxidizing agent.

Moreover, the resin composition of the present invention may also be prepared by further blending a compound represented by the following formula (5).

[Chemical Formula 3]

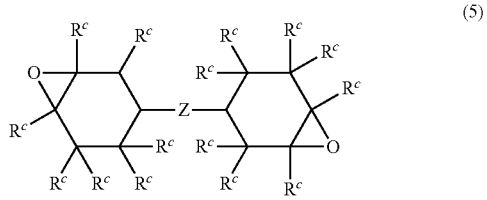

(5)

[In the formula, $R^c$ represents a hydrogen atom, a halogen atom, an alkyl group which may have a substituent, or an alkoxy group which may have a substituent, and Z represents a linking group. A plurality of $R^c$s may be the same or different from each other.]

The present invention also provides a cured resin product obtained by curing the above resin composition. The cured resin product of the present invention has a sufficient optical transparency to light other than visible light as well.

The present invention also provide a photosemiconductor device sealed with the above resin composition.

The present invention also relates to a method for producing an epoxy compound comprising: an oxidation step of obtaining an epoxy compound represented by the following formula (1) through an oxidation reaction of a compound represented by the following formula (2); and a purification step of purifying the above epoxy compound obtained by the above oxidation step in such a way that, in a chromatogram obtained by gas chromatographic analysis, a ratio of a peak area B of peaks derived from a heavier molecular mass portion having longer retention times than the above epoxy compound to a peak area A of peak(s) derived from the above epoxy compound B/A is $2.0 \times 10^{-3}$ or less.

[Chemical Formula 4]

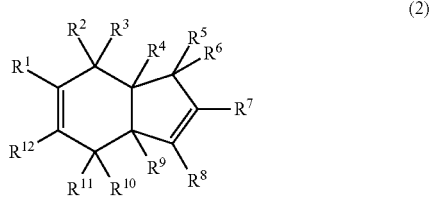

(2)

[Chemical Formula 5]

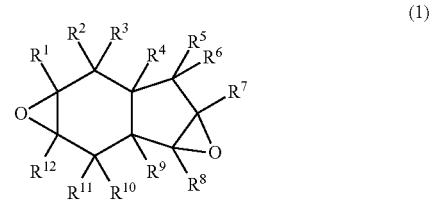

(1)

[In the formula, $R^1$, $R^2$, $R^3$, $R^4$, $R^5$, $R^6$, $R^7$, $R^8$, $R^9$, $R^{10}$, $R^{11}$, and $R^{12}$ each independently represent a hydrogen atom, a halogen atom, an alkyl group which may have a substituent, or an alkoxy group which may have a substituent.]

In the method for producing the epoxy compound of the present invention, the compound represented by the above formula (2) is preferably a compound represented by the following formula (2-1), and the epoxy compound represented by the above formula (1) is preferably a compound represented by the following formula (1-1).

[Chemical Formula 6]

(2-1)

[Chemical Formula 7]

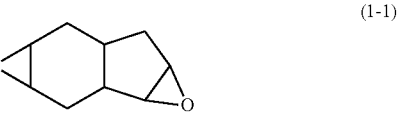

(1-1)

Advantageous Effects of Invention

According to the present invention, a cured alicyclic epoxy resin product having a sufficient optical transparency to not only visible light but also ultraviolet light, a resin composition for obtaining the cured resin product, and a photosemiconductor device sealed by using the resin composition are provided.

BRIEF DESCRIPTION OF DRAWINGS

FIG. 1 A figure showing a chromatogram obtained by gas chromatographic analysis of the (A-1) component obtained from Synthesis Example 1.

FIG. 2 A figure showing a chromatogram obtained by gas chromatographic analysis of the (A-5) component obtained from Synthesis Example 1.

DESCRIPTION OF EMBODIMENTS

Hereinafter, preferred embodiments of the resin composition of the present invention will be described.

The resin composition relating to the present embodiment is the resin composition prepared by blending an epoxy compound represented by the following formula (1) (hereinafter, referred to as an "(A) component" according to circumstances), an acid anhydride (hereinafter, referred to as a "(B) component" according to circumstances), and a curing accelerator (hereinafter, referred to as a "(C) component" according to circumstances), wherein the (A) component is purified in such a way that, in a chromatogram obtained by gas chromatographic analysis, a ratio of a peak area B of peaks derived from a heavier molecular mass portion having longer retention times than the (A) component to a peak area A of peak(s) derived from the (A) component B/A is $2.0 \times 10^{-3}$ or less (preferably, $1.3 \times 10^{-3}$ or less).

[Chemical Formula 8]

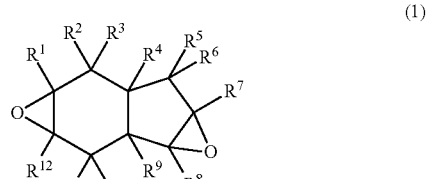

(1)

[In the formula, $R^1$, $R^2$, $R^3$, $R^4$, $R^5$, $R^6$, $R^7$, $R^8$, $R^9$, $R^{10}$, $R^{11}$, and $R^{12}$ each independently represent a hydrogen atom, a halogen atom, an alkyl group which may have a substituent, or an alkoxy group which may have a substituent.]

According to the resin composition relating to the present embodiment, a cured resin product having a sufficient optical transparency to not only visible light but also ultraviolet light can be obtained.

Moreover, the alicyclic epoxy resin described in Patent Literature 1 has an ester group within the molecule, therefore, has a hydrolyzability, and the deterioration of the physical properties of the cured product sometimes occurs for use under a high temperature and high humidity, or under the condition that a strong acid is generated, or the like. In contrast, the cured product of the above resin composition is excellent in heat resistance, humidity resistance, and acid resistance.

In addition, it is a thermosetting resin composition used as a substitute for a glass substrate used for liquid crystal panels or the like that is described in Patent Literature 3, optical transparency to light other than visible light (ultraviolet light, for example, such as UV-A (315 to 400 nm)) is not necessarily needed in such a field. Therefore, in Patent Literature 3, an evaluation of optical transparency for light other than visible light is not conducted, and any suggestion to obtain transparency for ultraviolet light is not made. Furthermore, in Patent Literature 3, an example in which a diepoxide of tetrahydroindene was used is described, however the example is inferior to other examples in optical transparency.

The case where the ratio of the (A) component, B/A exceeds $2.0 \times 10^{-3}$, the optical transparency to light around 800 nm of the cured resin product, for example, is good, however the optical transparency to UV-A (315 to 400 nm) decreases remarkably. In contrast, according to the above resin composition, a cured resin product having a sufficient optical transparency to not only visible light but also ultraviolet light (UV-A, for example) can be obtained.

$R^1$, $R^2$, $R^3$, $R^4$, $R^5$, $R^6$, $R^7$, $R^8$, $R^9$, $R^{10}$, $R^{11}$, and $R^{12}$ in the formula (1) each independently represent a hydrogen atom, a halogen atom, an alkyl group which may have a substituent, or an alkoxy group which may have a substituent.

As an alkyl group, an alkyl group having 1 to 10 carbon atoms is preferable, and an alkyl group having 1 to 4 carbon atoms is more preferable. When the alkyl group has a substituent, examples of the substituent include a halogen atom and an alkoxy group.

As an alkoxy group, an alkoxy group having 1 to 10 carbon atoms is preferable, and an alkoxy group having 1 to 4 carbon atoms is more preferable. When the alkoxy group has a substituent, examples of the substituent include a halogen atom and an alkoxy group.

$R^1$, $R^2$, $R^3$, $R^4$, $R^5$, $R^6$, $R^7$, $R^8$, $R^9$, $R^{10}$, $R^{11}$, and $R^{12}$ (1) each independently are preferably a hydrogen atom, a fluorine atom, an alkyl group, or an alkoxy group, more preferably a hydrogen atom or a fluorine atom, even more preferably a hydrogen atom.

Thus, as an (A) component, a compound represented by the following formula (1-1) can particularly preferably be used.

[Chemical Formula 9]

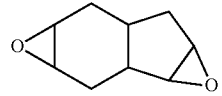

(1-1)

The gas chromatographic analysis can be carried out under the following conditions.

Equipment used: 6850 Series manufactured by Agilent Technologies, Inc.

Column: Agilent 19091Z-413E (HP-1 dimethylpolysiloxane, capillary 30.0 m×320 μm×0.25 μm)

Inlet: 250° C.

Detector: 250° C.

Oven: 50° C. (10 min), 250° C. (5° C./min), 250° C. (20 min)

The (A) component may be a mixture of stereoisomers. When the (A) component is a mixture of stereoisomers, the peak area A indicates the total area of peaks derived from respective stereoisomers. Moreover, when the (A) component is a mixture of stereoisomers, "the retention time longer than that of the (A) component" indicates that the retention time is longer than the longest retention time among the retention times of stereoisomers of the (A) component.

FIG. 1 and FIG. 2 are figures showing a chromatogram obtained by gas chromatographic analysis of the epoxy compound obtained from Synthesis Example 1 described later, and in FIG. 1 and FIG. 2, the peaks designated as a-1, a-2, a-3, and a-4 are the peaks derived from the (A) component, and the peak in the range designated as b is the peak derived from the heavier molecular mass portion.

In addition, the analysis of each peak can be carried out by the gas chromatography-mass spectrometry analysis under the following conditions.
(a) Gas Chromatography Part Equipment used: 7890A manufactured by Agilent Technologies, Inc.

Column: Agilent 19091S-936 (HP-1MS dimethylpolysiloxane, capillary 60.0 m×250 μm×0.25 μm)

Inlet: 250° C.

Oven: 40° C. (10 min), 300° C. (5° C./min), 300° C. (18 min)
(b) Mass Spectrometry Analysis Part Equipment used: 5975C VL MSD manufactured by Agilent Technologies, Inc.

Ionization method: Electron impact ionization technique

Temperature of ion source: 230° C.

Temperature of MS quadrupole: 150° C.

For example, when the gas chromatography-mass spectrometry analysis is carried out for the epoxy compound of the Synthesis Example 1 described later, the peaks derived from a compound having a molecular weight of 152 are observed as the peaks corresponding to the peaks designated as a-1, a-2, a-3, and a-4 in FIG. 1 and FIG. 2. From this, the peaks designated as a-1, a-2, a-3, and a-4 can be confirmed to be the peaks derived from the (A) component. Moreover, the peaks derived from to the compound of a heavier molecular mass portion having a molecular weight of 155 to 168 are observed as the peaks corresponding to the peaks in the range designated as b in FIG. 1 and FIG. 2.

The (A) component can be produced by the following method comprising an oxidizing step and a purification step.

In the oxidation step, the (A) component is synthesized through the oxidation reaction of a compound represented by the following formula (2).

[Chemical Formula 10]

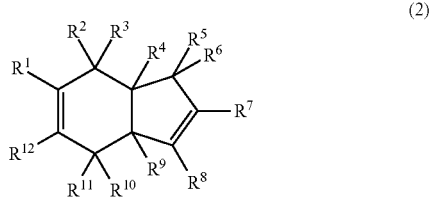

(2)

The method of oxidation reaction is not specifically limited and can be carried out, for example, by the method described in Japanese Patent Application Laid-Open No. 2004-182648.

Moreover, the oxidation reaction can also be carried out by the method in which an epoxy compound is produced from a conventionally known olefin compound. Examples of such a method include, for example, a method described in J. Org. Chem. 2000, 65, 8651, a method described in Organic Syntheses, 1997, 74, 91, a method described in Organic Syntheses, Coll. 1998, 9, 288, and so on.

Moreover, specific examples of the oxidation reaction include a method in which the reaction is carried out by adding 30% hydrogen peroxide water to a dichloromethane solution containing a compound represented by the formula (2), pyridine, 3-cyanopyridine and methyltrioxorhenium at room temperature (25° C.).

In the purification step, the (A) component obtained by the above oxidation step is purified in such a way that, in a chromatogram obtained by the gas chromatographic analysis, a ratio of a peak area B of peaks derived from a heavier molecular mass portion having longer retention times than the (A) component to a peak area A of peak(s) derived from the (A) component B/A is $2.0 \times 10^{-3}$ or less.

A purification method of the (A) component is not specifically limited as long as the method is the one by which the ratio B/A is $2.0 \times 10^{-3}$ or less, and examples of the purification method include, for example, a purification by distillation.

Since an (A) component is a thermally unstable compound, there sometimes occurs a case where a part of an (A) component is decomposed or a heavier molecular mass portion is produced when a temperature in the purification by distillation is too high or the retention time is too long. Therefore, it is preferable that the temperature in the purification by distillation is set to 20 to 150° C. and the retention time is set to 0.01 to 60 minutes. Examples of a distillation apparatus include, for example, a batch system precision distillation apparatus, a centrifugal molecular distillation apparatus, a thin film distillation apparatus, and so on.

More specifically, the purification by distillation can be carried out, for example, at 600 Pa in a column bottom temperature range of 30 to 80° C. and in such a way that fractions of distillation flowed out are fractionated in sequence, and the fraction of distillation in which the ratio B/A is $2.0 \times 10^{-3}$ or less is extracted.

A chlorine content of the (A) component is preferably 100 ppm or less, more preferably 10 ppm or less because the reliability in terms of humidity resistance of the cured resin product becomes further improved and more suitable for the use of sealing photosemiconductors. In addition, the chlorine content is a value measured in conformity to JIS standard K-7243-3, specifically the value measured by dissolving the (A) component in diethylene glycol monobutyl ether, saponificating the (A) component with an alcohol solution of potassium hydroxide under heating and refluxing, and carrying out a potentiometric titration of a silver nitrate solution.

The chlorine content of the (A) component can be reduced by the above described purification by distillation and can also be reduced by a method such as a cleaning with an aqueous alkaline solution, a processing with an adsorbent, or the like.

A metal content of the (A) component is preferably 100 ppm or less, more preferably 10 ppm or less because the mechanical and electrical properties of the cured resin product become further improved and more suitable for the use of sealing photosemiconductors. In addition, the metal content can be measured by carrying out inductively coupled plasma emission (ICP emission) spectrometric analysis of a 10% toluene solution of the (A) component. As a measuring apparatus, Optima 4300DV manufactured by PerkinElmer, Inc., for example, can be used. In this measurement, as for metal species detected by a qualitative analysis, a quantitative analysis can be carried out with a calibration curve made by using respective commercial metal standard solutions.

The metal content of the (A) component can be reduced by the above described purification by distillation and can also be reduced by a method such as a cleaning with an aqueous alkaline solution, a processing with an adsorbent, or the like.

A blending amount of the (A) component is preferably 12 to 45 mass %, more preferably 14 to 38 mass % based on the total mass of the resin composition.

The acid anhydride of the (B) component is a component that reacts with the epoxy compound in the resin composition to cure the resin composition. Examples of the (B) component include phthalic anhydride, maleic anhydride, trimellitic anhydride, pyromellitic anhydride, hexahydrophthalic anhydride, methylhexahydrophthalic anhydride, tetrahydrophthalic anhydride, methyltetrahydrophthalic anhydride, methyl-endoethylenetetrahydrophthalic anhydride, trialkyltetrahydrophtalic anhydride, methylnadic anhydride, nadic anhydride, and glutaric anhydride.

A blending amount of the (B) component is preferably 45 to 320 parts by mass with respect to 100 parts by mass of a blending amount of the epoxy compound in the resin composition, more preferably 70 to 250 parts by mass. In more detail, the blending amount of the (B) component is preferably an effective amount by which the effect as a curing agent can be exhibited, specifically 0.6 to 1.5 equivalents, more preferably 0.8 to 1.2 equivalents with respect to 1 epoxy equivalent of the epoxy compound in the resin composition.

The curing accelerator of the (C) component is a component that accelerates the reaction of the epoxy compound in the resin composition with the (B) component and accelerates the curing of the resin composition. Examples of the (C) component include tertiary amines, imidazoles, metal salts of carboxylic acids, and phosphorus compounds.

Examples of the tertiary amines include benzyl dimethyl amine, 2,4,6-tris(dimethylaminomethyl)phenol, 1,8-diazabicyclo[5.4.0]undecene-7, and 1,5-diazabicyclo[4.3.0]nonene-5. Moreover, examples of imidazoles include 2-methylimidazole, and 2-ethyl-4-methylimidazole.

Examples of metal salts of carboxylic acids include zinc octylate, and tin octylate. Moreover, examples of phosphorus compounds include tetraphenylphosphonium bromide, and tetra-n-butylphosphonium o,o-diethyl phosphorodithioate.

A blending amount of the (C) component is preferably 0.1 to 5 parts by mass, more preferably 0.2 to 2 parts by mass with respect to 100 parts by mass of the epoxy compound blended in the resin composition.

The resin composition may be blended with a component except the above components. For example, the resin composition may further be blended with an antioxidizing agent (hereinafter, referred to as a "(D) component" according to circumstances).

Examples of a (D) component include a phenolic antioxidant, a sulphur type antioxidant, and a phosphorous type antioxidant.

Examples of a phenolic antioxidant include, for example, monophenols such as 2,6-di-t-butyl-p-cresol (BHT), butylated hydroxyanisole, 2,6-di-t-butyl-p-ethylphenol, and stearyl-β(3,5-di-t-butyl-4-hydroxyphenyl)propionate; bisphenols such as 2,2'-methylenebis(4-methyl-6-t-butylphenol), 2,2'-methylenebis(4-ethyl-6-t-butylphenol), 4,4'-thiobis(3-methyl-6-t-butylphenol), 4,4'-butylidenebis(3-methyl-6-t-butylphenol), and 3,9-bis[1,1-dimethyl-2-{β-(3-t-butyl-4-hydroxy-5-methylphenyl)propionyloxy}ethyl]2,4,8,10-tetraoxaspiro[5.5]undecane; 1,1,3-tris(2-methyl-4-hydroxy-5-t-butylphenyl) butane, 1,3,5-trimethyl-2,4,6-tris(3,5-di-t-butyl-4-hydroxybenzyl)benzene, tetrakis-[methylene-3-(3',5'-di-t-butyl-4'-hydroxyphenyl)propionate]methane, bis[3,3'-bis-(4'-hydroxy-3'-t-butylphenyl)butyric acid]glycol ester, and 1,3,5-tris(3',5'-di-t-butyl-4'-hydroxybenzyl)-s-triazine-2,4,6 (1H,3H,5H)trione, tocophenol.

Examples of a sulphur type antioxidant include dilauryl-3,3'-thiodipropionate, and distearyl-3,3'-thiodipropionate.

Examples of a phosphorous type antioxidant include phosphites such as triphenyl phosphite, tridecyl phosphite, diphenyl isodecyl phosphite, phenyl diisodecyl phosphite, tris(nonylphenyl)phosphite, diisodecyl pentaerythritol phosphite, tris(2,4-di-t-butylphenyl)phosphite, cyclic neopentane-tetra-ylbis(octadecyl)phosphite, cyclic neopentane-tetra-ylbis(2,4-di-t-butylphenyl)phosphite, cyclic neopentane-tetra-ylbis(2,4-di-t-butyl-4-methylphenyl) phosphite, and bis[2-t-butyl-6-methyl-4-{2-(octadecyloxycarbonyl)ethyl}phenyl]hydrogen phosphite; oxaphosphaphenanthrene oxides such as 9,10-dihydro-9-oxa-10-phosphaphenanthrene-10-oxide, and 10-(3,5-di-t-butyl-4-hydroxybenzyl)-9,10-dihydro-9-oxa-10-phosphaphenanthrene-10-oxide; and the like.

A blending amount of the (D) component is preferably 0.01 to 5 parts by mass, more preferably 0.1 to 4 parts by mass with respect to 100 parts by mass of the blending amount of the epoxy compound in the resin composition.

Moreover, the resin composition may further be blended with an epoxy compound except the (A) components (hereinafter, referred to as an "(A') component according to circumstances).

Examples of the (A') component include, for example, a compound having an alicyclic epoxy group. Examples of the compound having an alicyclic epoxy group include, for example, a compound represented by the following formula (3), a compound represented by the following formula (4), and a compound represented by the following formula (5).

[Chemical Formula 11]

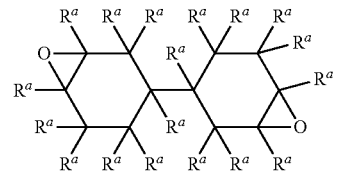

(3)

[Chemical Formula 12]

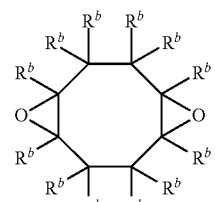

(4)

[Chemical Formula 13]

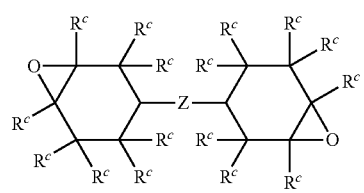

(5)

In the formula (3), $R^a$ represents a hydrogen atom, a halogen atom, an alkyl group which may have a substituent, or an alkoxy group which may have a substituent, and a plurality of $R^a$s may be the same or different from each other. $R^a$ is preferably a hydrogen atom, a fluorine atom, an alkyl group, or an alkoxy group, more preferably a hydrogen atom or a fluorine atom, even more preferably a hydrogen atom. In addition, as examples of an alkyl group and an alkoxy group in $R^a$, the same groups as the alkyl groups and an alkoxy groups as in $R^1$ to $R^{12}$ can be illustrated.

In the formula (4), $R^b$ represents a hydrogen atom, a halogen atom, an alkyl group which may have a substituent, or an alkoxy group which may have a substituent, and a plurality of $R^b$s may be the same or different from each other. $R^b$ is preferably a hydrogen atom, a fluorine atom, an alkyl group, or an alkoxy group, more preferably a hydrogen atom or a fluorine atom, even more preferably a hydrogen atom. In addition, as examples of an alkyl group and an alkoxy group in $R^b$, the same groups as the alkyl groups and an alkoxy groups as in $R^1$ to $R^{12}$ can be illustrated.

In the formula (5), $R^c$ represents a hydrogen atom, a halogen atom, an alkyl group which may have a substituent, or an alkoxy group which may have a substituent, and Z represents a linking group. A plurality of $R^c$s may be the same or different from each other. $R^c$ is preferably a hydrogen atom, a fluorine atom, an alkyl group, or an alkoxy group, more preferably a hydrogen atom or a fluorine atom, even more preferably a hydrogen atom. In addition, as examples of an alkyl group and an alkoxy group in $R^c$, the same groups as the alkyl groups or an alkoxy groups as in $R^1$ to $R^{12}$ can be illustrated.

Examples of a linking group include a single bond, a bivalent hydrocarbon group, a carbonyl group (—CO—), an ether linkage (—O—), an ester linkage (—COO—), an amide linkage (—CONH—), a carbonate linkage (—OCOO—), and a group in which a plurality of these linking groups are linked.

It is preferable that the number of carbon atoms in the above bivalent hydrocarbon group is 1 to 18. Moreover, it is preferable that the above bivalent hydrocarbon group is a straight or branched chain alkylene group, a bivalent alicyclic hydrocarbon group (a cycloalkylene group, in particular), or the like. Examples of an alkylene group include a methylene group, a methylmethylene group, dimethylmethylene group, an ethylene group, a propylene group, and a trimethylene group. Moreover, examples of a bivalent alicyclic hydrocarbon group include a 1,2-cyclopenthylene group, a 1,3-cyclopenthylene group, a cyclopentylidene group, a 1,2-cyclohexylene group, a 1,3-cyclohexylene group, a 1,4-cyclohexylene group, and a cyclohexylidene group.

Specific examples of the compound represented by the formula (5) include compounds represented by the following formula (5-1) to (5-7).

[Chemical Formula 14]

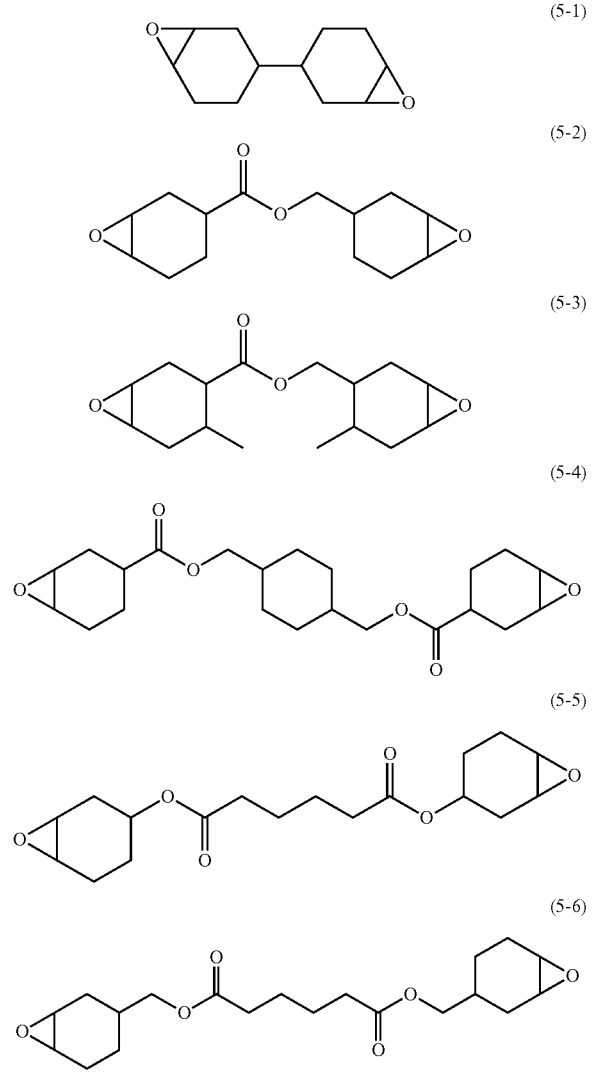

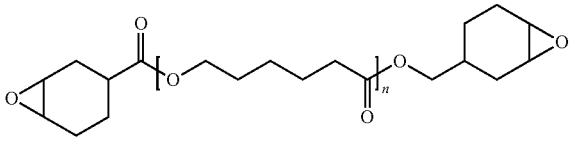

Moreover, examples of the compound having an alicyclic epoxy group may also include dicyclopentadiene dioxide, limonene dioxide, di(3,4-epoxycyclohexyl)adipate, 3,4-epoxycyclohexylmethyl-3',4'-epoxycyclohexane carboxylate (Celloxide 2021P (manufactured by Daicel Chemical Industries, Ltd.) etc. as a commercial product), (3,4-epoxy-6-methyl-cyclohexyl)methyl-3,4-epoxy-6-methylcyclohexane carboxylate, and ethylene-1,2-di(3,4-epoxycyclohexane carboxylic acid) ester.

As the compound having an alicyclic epoxy group, among the above compounds, the compound represented by the formula (3), the compound represented by the formula (4), the compound represented by the formula (5) (3,4-epoxycyclohexylmethyl-3',4'-epoxycyclohexane carboxylate, in particular), 3,4-epoxycyclohexyl methyl alcohol, and 3,4-epoxycyclohexylethyltrimethoxy silane can preferably be used.

Moreover, a compound having an epoxy group except alicyclic epoxy groups can also be used as the (A') component. Examples of such a compound include diglycidyl ethers of various bisphenol types as typified by bisphenol-A type and bisphenol-F type (Epikote 828, 806 (manufactured by Japan Epoxy Resins Co., Ltd.), YD-128 (manufactured by Tohto Kasei Co., Ltd.), etc. as commercial products); nuclear hydrogenation products of bisphenol type epoxy resins (HBE-100 (manufactured by New Japan Chemical Co., Ltd.), YX-4000, YX-8000 (manufactured by Japan Epoxy Resins Co., Ltd.), etc. as commercial products); glycidyl ethers having a cyclic aliphatic skeleton such as a diglycidyl ether of cyclohexanedimethanol (DME-100 (manufactured by New Japan Chemical Co., Ltd.), etc. as a commercial product); glycidyl ethers of novolac type phenol resins; glycydyl ethers of novolac type phenol resins in which DCPD (dicyclopentadiene) or the like is copolymerized: glycidyl ethers of polycyclic aromatic compounds such as naphthalene; epoxy resins having a terminal epoxy group in a cycloaliphatic skeleton (EHPE-3150, EHPE-3150CE (manufactured by Daicel Chemical Industries, Ltd.), etc. as commercial products); and silicone resins having an epoxy group (A-186 (manufactured by Nippon Unicar Co., Ltd.), KBM303, KBM403, KBM42 (manufactured by Shin-Etsu Chemical Co., Ltd.) etc. as commercial products).

The (A') component can be used alone or in combination of two or more kinds.

When the (A') component is blended, the ratio of the blending amount A' of (A') component to the blending amount A of the (A) component A'/A (mass ratio) can be set to 1/99 to 99/1 and may also be set to 1/99 to 90/10.

Furthermore, the resin composition may further be blended with an additive such as a UV absorber or the like as a component except the above components.

The resin composition relating to the present embodiment is cured by heating to form a cured resin product. The cured resin product thus formed has a sufficient optical transparency to not only visible light but also light other than visible light (for example, ultraviolet light such as UV-A (315 to 400 nm)). Therefore, the resin composition relating to the present embodiment can preferably be used for the use in which the optical transparency of the cured products is necessary such as a sealing material or the like to seal a photosemiconductor element.

Moreover, a photosemiconductor device can be obtained by casting the resin composition relating to the present embodiment into a predetermined forming die, carrying out a heat curing under a predetermined condition, and sealing a photosemiconductor element. Such a photosemiconductor device protects a peripheral part of an emitter by using the resin composition relating to the present embodiment as a sealing material, and, therefore, is useful as the photosemiconductor device with a high reliability without a problem such as the reduction in luminance by yellowing, discoloration, or the like.

Preferred embodiments of the present invention are described above, however the present invention is not limited to the above embodiments.

EXAMPLES

Hereinafter, the present invention will be described more specifically with reference to Examples, however the present invention is not limited to these Examples.

Synthesis Example 1

120 g of tetrahydroindene, 15.8 g of pyridine, 20.8 g of 3-cyanopyridine, 2.49 g of methyltrioxorhenium, 440 g of dichloromethane, and 450 g of 30% hydrogen peroxide water were charged in this order into a reaction vessel in which a stirring apparatus is installed. After stirring the resultant mixture at room temperature for 2 hours, an oil phase and a waterphase were separated. The water phase was washed by adding 200 g of dichloromethane to the water phase and stirring. An oil phase generated by the washing operation and the former oil phase were mixed, and the solvent was evaporated with a rotary evaporator to obtain a crude product.

The obtained crude product was distilled under the condition of 220 Pa and 0° C. to obtain 143 g of the epoxy compound represented by the above formula (1). Gas chromatographic analysis was carried out for the obtained epoxy compound to find out that a ratio of a peak area B of peaks derived from the heavier molecular mass portion having longer retention times than the epoxy compound to a peak area A of peak(s) derived from the epoxy compound B/A was $5.7 \times 10^{-3}$. This epoxy compound was designated as an (A-5) component.

Next, 100 g of the (A-5) component was charged into a precision distiller, and the precision distillation was carried out under the condition of 600 Pa and a column bottom temperature range of 30 to 80° C. to fractionate the fractions flowed out in sequence. Gas chromatographic analysis was carried out for the four fractionated fractions to find out that a ratio B/A is $1.0 \times 10^{-3}$, $1.1 \times 10^{-3}$, $1.6 \times 10^{-3}$, and $3.0 \times 10^{-3}$, respectively. These four fractions were designated as an (A-1) component, an (A-2) component, an (A-3) component, and an (A-4) component, respectively. A distillation yield of the (A-1) component was 20 g, a distillation yield of the (A-2) component was 20 g, a distillation yield of the (A-3) component was 20 g, and a distillation yield of the (A-4) component was 35 g with respect to 100 g of the (A-5) component. These results are shown in Table 1.

In addition, the gas chromatographic analysis was carried out under the conditions shown below.

Equipment used: 6850 Series manufactured by Agilent Technologies, Inc.
Column: Agilent 19091Z-413E (HP-1 dimethylpolysiloxane, capillary 30.0 m×320 μm×0.25 μm)
Inlet: 250° C.
Detector: 250° C.
Oven: 50° C. (10 min), 250° C. (5° C./min), 250° C. (20 min)

FIG. 1 is a figure showing a chromatogram obtained by the gas chromatographic analysis of the (A-1) component, and FIG. 2 is a figure showing a chromatogram obtained by the gas chromatographic analysis of the (A-5) component.

TABLE 1

|  | Distillation yield (%) | Ratio B/A ($\times 10^{-3}$) |
| --- | --- | --- |
| (A-1) component | 20 | 1.0 |
| (A-2) component | 20 | 1.1 |
| (A-3) component | 20 | 1.6 |
| (A-4) component | 35 | 3.0 |
| (A-5) component | — | 5.7 |

The light transmittances (%) at a wavelength of 350 nm, 400 nm, and 800 nm for the (A-1) to the (A-5) component were measured with a spectrophotometer (V-570: manufactured by JASCO Corporation). Measurement results were as described in Table 2.

TABLE 2

|  | (A-1) component | (A-2) component | (A-3) component | (A-4) component | (A-5) component |
| --- | --- | --- | --- | --- | --- |
| 350 nm | 95 | 95 | 94 | 92 | 88 |
| 400 nm | 99 | 99 | 99 | 99 | 99 |
| 800 nm | 99 | 99 | 99 | 99 | 99 |

Examples 1 to 3, Comparative Examples 1 to 2

Respective raw materials were blended by an amount of parts (parts by mass) as shown in Table 3 and Table 4, and a resin composition in liquid form was obtained by stirring at room temperature. Celloxide 2021P (manufactured by Daicel Chemical Industries, Ltd., 3,4-epoxycyclohexylmethyl-3',4'-epoxycyclohexane carboxylate) was used as an (A') component, Rikasid MH-700 (manufactured by New Japan Chemical Co., Ltd., 4-methylhexahydro phthalic anhydride/hexahydro phthalic anhydride=70/30) was used as an acid anhydride, Hishicolin PX-4ET (manufactured by Nippon Chemical Industrial Co., LTD., tetra-n-butyl phosphonium o,o-diethyl phosphorodithioate) was used as a curing accelerator, and 2,6-di-t-butyl-p-cresol (represented as "BHT" in Tables 3 and 4) and triphenyl phosphite (represented as "TPP" in Tables 3 and 4) were used as an antioxidizing agent.

TABLE 3

|  | Example 1 | Example 2 | Example 3 | Comparative Example 1 | Comparative Example 2 |
| --- | --- | --- | --- | --- | --- |
| (A-1) component | 100 | — | — | — | — |
| (A-2) component | — | 100 | — | — | — |
| (A-3) component | — | — | 100 | — | — |

TABLE 3-continued

|  |  | Example 1 | Example 2 | Example 3 | Comparative Example 1 | Comparative Example 2 |
|---|---|---|---|---|---|---|
| (A-4) component | | — | — | — | 100 | — |
| (A-5) component | | — | — | — | — | 100 |
| Acid anhydride | | 187 | 187 | 187 | 187 | 187 |
| Curing accelerator | | 0.50 | 0.50 | 0.50 | 0.50 | 0.50 |
| Antioxidizing agent | BHT | 0.20 | 0.20 | 0.20 | 0.20 | 0.20 |
|  | TPP | 0.20 | 0.20 | 0.20 | 0.20 | 0.20 |

TABLE 4

|  |  | Example 4 | Example 5 | Example 6 | Example 7 |
|---|---|---|---|---|---|
| (A-1) component | | 80 | 60 | 40 | — |
| (A-2) component | | — | — | — | 80 |
| (A-3) component | | — | — | — | — |
| (A') component | | 20 | 40 | 60 | 20 |
| Acid anhydride | | 172 | 158 | 144 | 172 |
| Curing accelerator | | 0.50 | 0.50 | 0.50 | 0.50 |
| Antioxidizing agent | BHT | 0.16 | 0.12 | 0.08 | 0.16 |
|  | TPP | 0.16 | 0.12 | 0.08 | 0.16 |

Next, the obtained resin composition was cast in an aluminum die of φ 60 mm×1 mm, and was cured by heating at 110° C. for 2 hours and at 120° C. for 5 hours to obtain a test piece of the cured resin product.

The obtained test piece was set in a spectrophotometer (V-570: manufactured by JASCO Corporation), and the light transmittances (%) at a wavelength of 350 nm, 400 nm, and 800 nm were measured. Measurement results were as described in Table 5 and Table 6.

TABLE 5

|  | Example 1 | Example 2 | Example 3 | Comparative Example 1 | Comparative Example 2 |
|---|---|---|---|---|---|
| 350 nm | 75 | 72 | 61 | 37 | 23 |
| 400 nm | 83 | 80 | 77 | 64 | 53 |
| 800 nm | 86 | 87 | 91 | 90 | 88 |

TABLE 6

|  | Example 4 | Example 5 | Example 6 | Example 7 |
|---|---|---|---|---|
| 350 nm | 73 | 71 | 70 | 71 |
| 400 nm | 82 | 81 | 81 | 80 |
| 800 nm | 87 | 88 | 89 | 88 |

As shown in Table 2 and Table 5, the light transmittances of the (A-1) to (A-5) components had no or little difference caused by the varying ratio B/A, but the light transmittances of the cured resin products for UV-A, which were produced using these components, were significantly different.

Specifically, as shown in Table 5 and Table 6, the cured resin products obtained from the resin compositions of Examples had a light transmittance at 350 nm of 70% or more, and a light transmittance at 400 nm of 80% or more, which indicates they had sufficiently high light transmittances better than those of the cured resin products of Comparative Examples. From this fact, it was confirmed that the resin composition of the present invention was useful as a sealing material for sealing a photosemiconductor element.

The invention claimed is:

1. A resin composition prepared by blending an epoxy compound represented by the following formula (1), an acid anhydride, and a curing accelerator, wherein the epoxy compound is purified in such a wa that, in a chromatogram obtained by gas chromatographic analysis, a ratio of a peak area B of peaks derived from a heavier molecular mass portion having longer retention times than the epoxy compound to a peak area A of peak(s) derived from the epoxy compound B/A is $2.0 \times 10^{-3}$ or less,

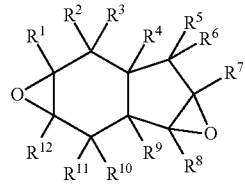

(1)

wherein $R^1$, $R^2$, $R^3$, $R^4$, $R^5$, $R^6$, $R^7$, $R^8$, $R^9$, $R^{10}$, $R^{11}$, and $R^{12}$ each independently represent a hydrogen atom, a halogen atom, an alkyl group which may have a substituent, or an alkoxy group which may have a substituent.

2. The resin composition according to claim 1, wherein the epoxy compound is a compound represented by the following formula (1-1)

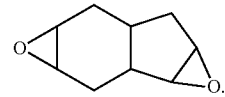

(1-1)

3. The resin composition according to claim 2, wherein the ratio B/A is $1.3 \times 10^{-3}$ or less.

4. The resin composition according to claim 1, prepared by further blending an antioxidizing agent.

5. The resin composition according to claim 1, prepared by further blending a compound represented by the following formula (5),

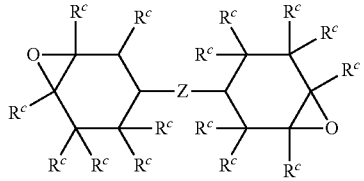

(5)

wherein $R^c$ represents a hydrogen atom, a halogen atom, an alkyl group which may have a substituent, or an alkoxy group which may have a substituent, and Z represents a linking group plurality of $R^c$s may be the same or different from each other.

6. A cured resin product obtained by curing a resin composition according to claim 1.

7. A photosemiconductor device sealed by using a resin composition according to claim 1.

8. The resin composition according to claim 1, wherein the ratio B/A is $1.3 \times 10^{-3}$ or less.

9. A method for producing an epoxy compound comprising:
obtaining an epoxy compound represented by the following formula (1) through oxidation reaction of a compound represented by the following formula (2); and
purifying the obtained epoxy compound in such a way that, in a chromatogram obtained by gas chromatographic analysis, a ratio of a peak area B of peaks derived from a heavier molecular mass portion having longer retention times than the epoxy compound to a peak area A of peak(s) derived from the epoxy compound B/A is $2.0 \times 10^{-3}$ or less,

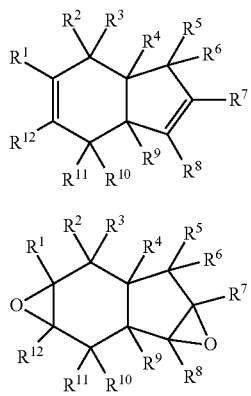

wherein $R^1$, $R^2$, $R^3$, $R^4$, $R^5$, $R^6$, $R^7$, $R^8$, $R^9$, $R^{10}$, $R^{11}$, and $R^{12}$ each independently represent a hydrogen atom, a halogen atom, an alkyl group which may have a substituent, or an alkoxy group which may have a substituent.

10. The method for producing an epoxy compound according to claim 9, wherein the compound represented by the formula (2) is a compound represented by the following formula (2-1), and the epoxy compound represented by the formula (1) is a compound represented by the following formula (1-1)

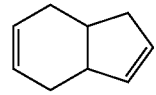

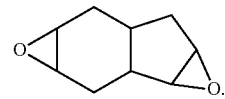

11. The method according to claim 10, wherein the ratio B/A is $1.3 \times 10^{-3}$ or less.

12. The method according to claim 10, wherein purifying comprises measuring the ratio B/A of at least a part of the epoxy compound.

13. The method according to claim 10, wherein purifying comprises distilling the obtained epoxy compound to obtain fractions fractionated in sequence and measuring the ratio B/A of at least a part of the fractions.

14. The method according to claim 10, wherein purifying comprises distilling the obtained epoxy compound at a temperature of 20 to 150° C.

15. The method according to claim 9, wherein the ratio B/A is $1.3 \times 10^{-3}$ or less.

16. The method according to claim 9, wherein purifying comprises measuring the ratio B/A of at least a part of the epoxy compound.

17. The method according to claim 9, wherein purifying comprises distilling the obtained epoxy compound to obtain fractions fractionated in sequence and measuring the ratio B/A of at least a part of the fractions.

18. The method according to claim 9, wherein purifying comprises distilling the obtained epoxy compound at a temperature of 20 to 150° C.

* * * * *

UNITED STATES PATENT AND TRADEMARK OFFICE
CERTIFICATE OF CORRECTION

PATENT NO. : 9,464,186 B2  
APPLICATION NO. : 14/009909  
DATED : October 11, 2016  
INVENTOR(S) : Kameyama et al.

Page 1 of 1

It is certified that error appears in the above-identified patent and that said Letters Patent is hereby corrected as shown below:

In the Claims

Column 16, Line 5 Claim 1, change "a wa" to -- a way --

Column 16, Line 60 Claim 5, change "R$^c$s may" to -- R$^c$s which may --

Signed and Sealed this  
Eighteenth Day of April, 2017

Michelle K. Lee  
*Director of the United States Patent and Trademark Office*